United States Patent [19]

Böhlendorf et al.

[11] Patent Number: 4,940,804
[45] Date of Patent: Jul. 10, 1990

[54] MICROBICIDES

[75] Inventors: Bettina Böhlendorf, Braunschweig; Norbert Bedorf, Königslutter; Gerhard Höfle; Dietmar Schummer, both of Braunschweig, all of Fed. Rep. of Germany; Marius Sutter, Basel, Switzerland

[73] Assignees: Gesellschaft für Biotechnologische Forschung mbH; Ciba-Geigy Corporation, Ardsley, N.Y.

[21] Appl. No.: 405,379

[22] Filed: Sep. 8, 1989

[30] Foreign Application Priority Data

Sep. 9, 1988 [CH] Switzerland .................. 3376/88

[51] Int. Cl.$^5$ ........................... C07D 321/00
[52] U.S. Cl. .................................. 549/267
[58] Field of Search ......................... 549/267

[56] References Cited

FOREIGN PATENT DOCUMENTS 0282455 9/1988 European Pat. Off. .

*Primary Examiner*—Glennon H. Hollrah
*Assistant Examiner*—Amelia A. Owens
*Attorney, Agent, or Firm*—George R. Dohmann; Edward McC. Roberts

[57] ABSTRACT

Derived macrocyclic compounds of the formula I

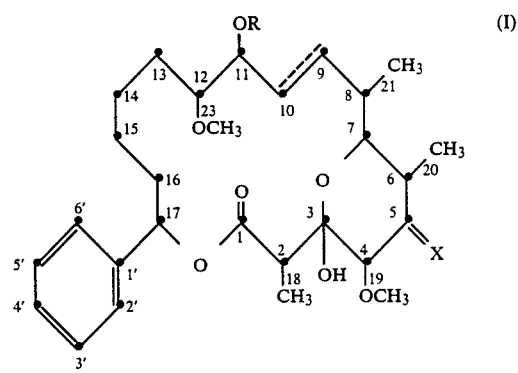

where R is hydrogen, methyl or certain acyl groups, the dotted line in the 9,10-position is a saturated bond or, in the event that R is methyl, is also a double bond, and X is a keto group, or a substituted or unsubstituted oxime, hydrazone or semicarbazone, represent effective microbicides for controlling plant diseases. They can be employed in the customary formulation as agrochemical agents.

9 Claims, No Drawings

MICROBICIDES

The present invention relates to a macrocyclic compound of the formula I, to a process for its preparation and to its use for the control of plant diseases, as well as to phytomicrobicidal agents containing this compound as the active substance.

[Structural formula I of macrocyclic compound with numbered positions, showing OR, OCH₃, CH₃ groups, phenyl ring, and X substituent]

In this formula, the dotted line in the 9,10-position is a saturated bond or a double bond, alternatively, while R is hydrogen, $CH_3$ or —COA, where A is hydrogen, $C_3$-$C_6$cycloalkyl or $C_1$-$C_6$alkyl which is unsubstituted or substituted by halogen or $C_1$-$C_3$alkoxy, and X is oxygen or one of the groups =N—OY or =N—N($R_1$)($R_2$), where Y is hydrogen, $C_1$-$C_6$alkyl, $C_3$-$C_6$alkenyl, $C_3$-$C_6$alkynyl or an acyl group —CO—Z in which Z is phenyl, or a $C_1$-$C_6$alkyl group which is substituted by halogen or $C_1$-$C_4$alkoxy, or is hydrogen, $C_1$-$C_6$alkyl, $C_2$-$C_6$alkenyl or $C_2$-$C_6$alkynyl;

$R_1$ is hydrogen or $C_1$-$C_6$alkyl and $R_2$ is hydrogen, $C_1$-$C_6$ alkyl, phenyl, carbamoyl(-CONH$_2$), —COA or —SO$_2$—R$_3$, where $R_3$ is $C_1$-$C_6$alkyl, or is phenyl which is unsubstituted or substituted by $C_1$-$C_4$alkyl;

with the proviso that R is methyl if there is a double bond in the 9,10-position.

In consequence, the preparations of the formula I represent 5-ketocompounds or, derived from these, 5-ketoximes, 5-hydrazones or 5-semicarbazone and certain acyl derivatives with carboxylic acids and sulfonic acids.

Depending on the chain length, alkyl is understood as meaning methyl, ethyl, propyl, butyl, amyl, hexyl, as well as their isomers, for example isopropyl, isobutyl, sec-butyl, tert-butyl, neopentyl etc.

A halogen-substituted alkyl radical is an alkyl substituent which is monohalogenated to perhalogenated, such as $CHCl_2$, $CH_2Cl$, $CCl_3$, $CF_3$, $C_2F_5$, $CH_2F$, $CH_2Br$, $CH_2CH_2Cl$, $CHF$-$CH_3$, $CHBr_2$ etc.

Halogen is understood as meaning fluorine, chlorine, bromine or iodine.

Examples of alkyl radicals which are monosubstituted or polysubstituted by alkoxy, also in the sense of an alkoxyalkoxy substitution, may be —CH$_2$OCH$_3$, —CH$_2$CH$_2$OCH$_3$, —CH$_2$CH(CH$_3$)OCH$_3$, —CH$_2$OC$_2$H$_5$, —CH$_2$OC$_3$H$_7$—i, —CH$_2$CH$_2$CH$_2$OCH$_3$, —CH$_2$OCH$_2$OCH$_3$, —CH$_2$CH$_2$OCH$_2$OCH$_3$, —CH$_2$OCH$_2$CH$_2$OCH$_3$, —CH$_2$OCH$_2$OC$_2$H$_5$, —C(CH$_3$)$_2$—CH$_2$OCH$_3$, —CH(CH$_3$)OCH$_2$OC$_3$H$_7$—i, —CH(OCH$_3$)—CH$_2$OCH$_3$ and other branched and unbranched radicals.

Alkenyl is an aliphatic hydrocarbon radical having a double bond, for example vinyl, propen-1-yl, allyl, buten-1-yl, buten-2-yl, hexen-2-yl etc.

Alkynyl is an aliphatic hydrocarbon radical having a triple bond, for example ethynyl, propyn-1-yl, propargyl, butyn-1-yl, hexyn-5-yl etc.

$C_3$-$C_6$cycloalkyl embraces the groups cyclopropyl, cyclobutyl, cyclopentyl and cyclohexyl.

The invention relates to compounds of the formula I in all possible stereoisomeric forms.

The compounds of the formula I are derived from the basic structure of novel macrocyclic compounds of the formula below which is called "soraphen A" and "soraphen B".

[Structural formula of soraphen parent compound with numbered positions]

In this formula, R is methyl if there is a double bond in the 9,10-position (=soraphen A), or R is hydrogen if there is a single bond in the 9,10-position (=soraphen B).

On the basis of the physicochemical data, it is assumed that the following configuration can be attributed to these two preparations:

[Stereochemical structure labeled "soraphen A" showing OCH₃ groups at positions 22, 23, CH₃ groups at 20, 21, OH groups, and phenyl ring]

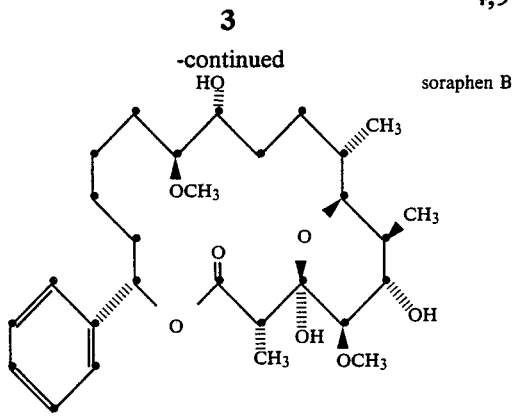

soraphen B

Soraphen A and B are derived by microbiological cultivation of a Sorangium (Polyangium) cellulosum strain "So ce 26". This strain was deposited on March 5, 1987, at the "National Collection of Industrial and Marine Bacteria (NCIB)", Torry Research Station, Aberdeen, Great Britain, and has the number NCIB 12 411 in accordance with the Budapest Convention. Sorangium cellulosum belongs to the order of the Myxobacterales, sub-order Sorangineae, family Polyangiaceae.

"So ce 26" itself or mutants or recombinants, are the subject-matter of European Patent Application EP-A-0,282,455. The strain can be cultured by customary biological methods, for example in shake cultures or in fermenters using nutrient media at a pH of 6-8 at 10-35° C. The process is aerobic. The conditions for the cultivation of the microorganism are introduced into the present description with reference to EP-A-0,282,455.

An important sub-group of compounds of the formula I is those in which R is hydrogen, $CH_3$ or —COA and X is oxygen. Here and below, this group will be designated sub-group IA.

From amongst the compounds of sub-group IA, those in which A is hydrogen or $C_1$-$C_3$alkyl which is unsubstituted or substituted by $C_1$-$C_3$alkoxy or monosubstituted or polysubstituted by fluorine or chlorine represent a special group (=sub-group IB). Another important sub-group is those of the formula I in which R is hydrogen, $CH_3$ or —COA, and X is the group =N—OY in which Y is hydrogen, $C_1$-$C_4$alkyl, $C_3$-$C_4$ alkenyl, $C_3$-$C_4$ alkynyl or —CO—Z, and Z is a $C_1$-$C_4$alkyl, $C_2$-$C_4$alkenyl or $C_3$-$C_4$alkynyl group, or is a $C_1$-$C_6$alkyl group which is substituted by fluorine, chlorine or methoxy (=sub-group IC).

Within sub-group IC, particular mention is made of those in which R is hydrogen, $CH_3$ or an acyl group —COA in which A is an unsubstituted or substituted radical having a maximum of 4 C atoms (=sub-group ICA).

Another important group within sub-group IC is those in which R is $CH_3$ and X is the group —N—OY in which Y is hydrogen, methyl, ethyl, isopropyl, allyl, propynyl, acetyl, trifluoroacetyl, trichloroacetyl or methoxyacetyl (=sub-group ICB).

A further important sub-group embraces those of the formula I in which R is hydrogen, $CH_3$ or —COA, and X is the group =N—N($R_1$)($R_2$) in which $R_1$ is hydrogen or $C_1$-$C_4$ alkyl and $R_2$ is hydrogen, $C_1$-$C_4$alkyl or phenyl (=subgroup ID). From amongst those of sub-group ID, particular mention is made of those in which R is $CH_3$ (=sub-group IDA).

Derivatives of compounds of the formula I can be formed in the 5- and 11-position, starting from "soraphen A" or "soraphen B" or "9,10-dihydrosoraphen A" by methods which are likewise the subject-matter of the present invention.

In "soraphen B", the reactivity of the hydroxyl group in the 5-position is different to that of the 11-position, and it can be oxidized in a directed manner to give the 5-keto group, with or without protective groups being employed. Furthermore, the 3-hydroxyl group in "soraphen A", in "soraphen B" as well as in "9,10-dihydrosoraphen A" is highly protected and accessible to chemical reactions with difficulty. "9,10-Dihydro- soraphen A" is obtained from "soraphen A" or a derivative protected in the 5-position by hydrogenation of the 9,10-double bond using homogeneous catalysts on the basis of transition metal complexes, for example rhodium complexes or iridium complexes. An example of a suitable complex is [iridium(cyclooctadiene)(acetonitrile)(tricyclohexylphosphine)]tetra-fluoroborate.

Here and below, these three starting materials for the compounds of the formula I shall be designated "soraphen", to simplify matters.

One of the subject-matters of the invention is a process for the preparation of compounds of the formula I in all possible stereoisomeric forms, which process comprises oxidising in a macrocyclic compound of the formula

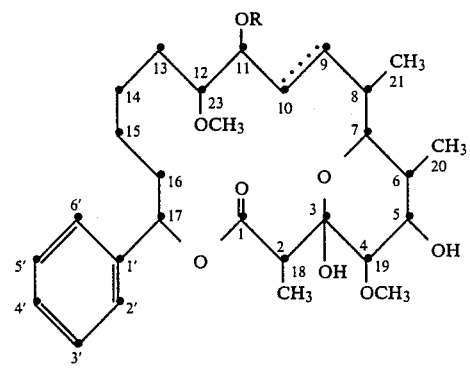

the OH group in the 5-position to the keto group in which formula functional groups are protected or unprotected and the dotted line in the 9,10-position is a saturated bond or a double bond, with the proviso that R is methyl if there is a double bond in the 9,10-position, and if desired, (a) oximizing the latter keto compound, and if desired, etherifying the oxime derivative by introducing substituent Y or acylating the oxime derivative by introducing —CO—Z, or (b) converting the keto group with a hydrazine derivative $H_2N$—$N(R_1)(R_2)$ into a hydrazone, or, if $R_2$ is carbamoyl, into a semicarbazone; with or without further acylation and/or elimination of protecting groups; the substituents mentioned having the meaning given in the case of formula I.

As already mentioned, the 5-hydroxyl group of "soraphen" may be oxidized to give the 5-keto group. Examples of possible oxidants are Cr(VI) compounds, such as pyridinium dichromate, pyridinium chlorochromate etc. The reaction is expediently carried out in a solvent which is inert towards the reaction. Examples of suitable solvents are ethers and ether-type compounds, such as dialkyl ethers (diethyl ether, diisopropyl ether, tert-butyl methyl ether, dimethoxyethane) dioxane, tetrahydrofuran (=THF), anisole, etc.; halogenated hydrocarbons, such as chlorobenzene, methylene chloride, ethylene chloride, chloroform, carbon tetrachloride, tetrachloroethylene, etc.; ketones, such as acetone; amides such as N,N-dimethylformamide; esters, such as ethyl acetate, propyl acetate, butyl acetate, etc.; as well as mixtures of the solvents with each other or with water and/or other customary inert solvents, such as benzene, xylene, petroleum ether, ligroin, cyclohexane. etc. In some cases it may be advantageous if the reaction, or part-steps thereof, are carried out under a protective gas atmosphere (for example argon, helium, nitrogen, etc.) and/or in absolute solvents. The reaction temperature is in the range from $-50°$ to $+50°$ C., preferably around $-10°$ to $+30°$ C.

Oximes and oxime ethers are obtained by reacting a 5-keto-soraphen with a primary oxamine of the formula $$H_2N—OY$$

or one of its salts, where Y has the abovementioned meaning and, in the event that Y is hydrogen and conversion into an oxime ether is intended, by subsequent reaction with a halide, preferably chloride or bromide, of the formula $$Hal—Y$$

where Y is $C_1$–$C_6$alkyl, $C_3$–$C_6$alkenyl or $C_3$–$C_6$alkynyl.

The preparation is carried out by reacting a 5-ketosoraphen with an oxamine at 10° to 100° C. in a suitable solvent, for example a lower alkanol, such as methanol, ethanol, propanol; an ether-type compound, such as tetrahydrofuran or dioxane; an aliphatic carboxylic acid, such as acetic acid or propionic acid; in water or in mixtures of these solvents with each other, or with other customary solvents which are inert towards the reaction.

If the oxamine is employed in the form of one of its salts, for example as the hydrochloride, it is advantageous to add a base for scavenging the acid, and, additionally, to carry out the process in the presence of a water binder, for example a molecular sieve. Possible bases which are suitable are organic and inorganic bases, for example tertiary amines, such as trialkylamines (trimethylamine, triethylamine, tripropylamine etc.), pyridine and pyridine bases (4-dimethylaminopyridine, 4-pyrrolidylaminopyridine etc.), oxides, hydrides and hydroxides, carbonates and hydrogen carbonates of alkali metals and alkaline earth metals (CaO, BaO, NaOH, KOH, NaH, Ca(OH)$_2$, KHCO$_3$, NaHCO$_3$, Ca(HCO$_3$)$_2$, K$_2$CO$_3$, Na$_2$CO$_3$), as well as alkali metal acetate.

Examples of suitable solvents for the further etherification are ethers and ether-type compounds, such as dialkyl ethers (diethyl ether, diisopropyl ether, tert-butyl methyl ether, dimethoxyethane, dioxane, tetrahydrofuran, anisole, etc.); halogenated hydrocarbons, such as chlorobenzene, methylene chloride, chloroform, carbon tetrachloride, tetrachloroethylene, etc.; sulfoxides, such as dimethyl sulfoxide, it being also possible for aromatic or aliphatic hydrocarbons, such as benzene, toluene, xylenes, petroleum ether, ligroin, cyclohexane, etc., to be present. In some cases, it may be advantageous to carry out the reactions under a protective gas atmosphere (for example argon, helium, nitrogen, etc.) and/or in absolute solvents. The reaction proceeds at 0° to 100° C., preferably at 10° to 60° C.

For scavenging the acid which has formed as a by-product, it is expedient to carry out the process in the presence of a neutralizing agent. Examples of possible agents are tertiary amines, such as trialkylamines (trimethyl amine, triethylamine, diisopropylethylamine, tripropylamine, etc.), pyridine and pyridine bases (4-dimethylaminopyridine, 4-pyrrollidylaminopyridine etc.). 5-O-Acylketoximes are obtained from the 5-ketoxime (=N—OH) following customary acylation methods which are also applicable to the acylation of an 11-hydroxy-soraphen (R=—COA), or for the acylation of a hydrazone described below (R$_2$=—COA or —SO$_3$R$_3$). The agent employed is the corresponding carboxylic acid or sulfonic acid, advantageously in excess, but preferably their acyl halides, in particular acyl bromides or acyl chlorides, in the case of the carboxylic acids also their acyl anhydrides.

O-Acylations are carried out in an anhydrous medium, preferably in inert solvents, and particularly preferably in aprotic solvents. The reaction advantageously proceeds in the temperature range of 0° C. to 80° C., preferably at 10° C. to 50° C. It is preferred to add an organic base. Examples of bases which may be mentioned are tertiary amines, such as triethylamine, triethylenediamine, triazole, preferably pyridine, imidazole or 1,8-diazabicyclo[5.4.0]undec-7-ene (DBU).

Examples of suitable solvents are: ethers and ether-type compounds, such as dialkyl ethers (diethyl ether, diisopropyl ether, tert-butyl methyl ether, dimethoxyethane, dioxane, tetrahydrofuran, anisole, etc.); halogenated hydrocarbons, such as chlorobenzene, methylene chloride, ethylene chloride, chloroform, carbon tetrachloride, tetrachloroethylene, etc.; or sulfoxides, such as dimethyl sulfoxide, it also being possible for aromatic or aliphatic hydrocarbons, such as benzene, toluene, xylenes, petroleum ether, ligroin, cyclohexane, etc., to be present. In some cases, it may be advantageous to carry out the reactions under a protective gas atmosphere (for example argon, helium, nitrogen, etc.) and/or in absolute solvents.

If a free carboxylic acid or sulfonic acid is employed as a reactant for the acylation, this reaction is expediently carried out in the presence of water-eliminating reagents. For example, the reaction is carried out in the presence of dicyclohexylcarbodiimide and pyridine, or in the presence of dialkyl azodicarboxylate and triphenyl phosphine.

If acid halides or acid anhydrides are employed for the acylation, the addition of a neutralizing agent proves to be advantageous. Reagents which are suitable are tertiary amines, such as trialkylamines, pyridine or pyridine bases, such as 4-dimethylaminopyridine, and some of them can also serve as the solvent.

5-Hydrazone derivatives of the formula I can be prepared from 5-ketosoraphen by reaction with a hydrazine derivative $$H_2N—N(R_1)(R_2)$$

or one of its salts with inorganic or organic acids, the process being carried out in the presence of a base, such as CaO, trialkylamine, Na acetate, pyridine, or, for acid catalysis, in the presence of an acid, such as acetic acid, hydrochloric acid or sulfuric acid. The reaction temperature is 0° to 100° C. Possible solvents are those which have been mentioned above, preferably water, alcohol, ethers, dioxane, benzene or glacial acetic acid.

If there are interfering functional groups in the molecule or in the reactant, such as OH, $NH_2$ or —COOH, these can initially be masked as already mentioned above, by acetylation or introduction of other protecting groups [T.W. Green "Protective Groups in Organic Synthesis", J. Wiley & Sons, 1981 (New York)].

The enumeration of all the previously mentioned methods is not by way of limitation. If desired, the end product can be purified in a customary manner, for example by washing, digesting, extraction, recrystallization, chromatography etc..

The preparation processes mentioned, including all part-steps, form part of the present invention.

It must be noted that the macrocyclic soraphens of the formula I are usually present in the hemiacetal form which is illustrated, but that this form can undergo reversible ring opening according to the equation

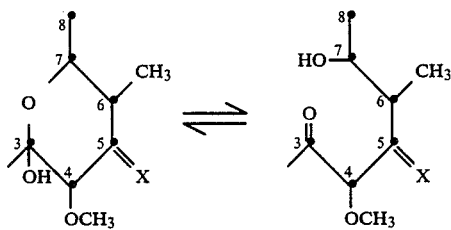

Depending on the preparation or working-up technique, the soraphens are obtained in one or the other form or as a mixture of both forms, depending on the pH and on the solvent. The shift of the $^{13}C$-NMR signal in the 3-position and that of the $^1H$-NMR signals in certain other positions is characteristic of the ring-opening. In the case of soraphen A, for example, the following modifications are observed: $^{13}C$-NMR(CDCl$_3$, $\delta$ in ppm) 99.5≧203.1(3-C).$^1H$-NMR(CDCl$_3$, $\delta$ in ppm): 3.14→3.72(2-H); 3.18→4.5(4-H); 3.83→3.16 (7-H); 5.86→5.7 (17-H). Similar shifts are also observed in the soraphen derivatives of the formula I described herein. Formula I of the present invention essentially embraces the 3-hemiacetal form, which is preferred in the lower pH range, and the opened 3-keto-7-hydroxy form.

It has been found that compounds of the formula I have a biocidal spectrum against phytopathogenic microorganisms, in particular against fungi, which is highly favourable for practical requirements. They have highly advantageous curative, systemic and in particular preventive properties and are employed for the protection of numerous crop plants. Using the active substances of the formula I, pests which occur on plants or parts of plants (fruits, flowers, foliage, stalks, tubers, roots) of various crops can be brought under control or destroyed, additional growth of parts of plants which occurs later also being kept free from phytopathogenic microorganisms.

As microbicides, the active substances of the formula I are active for example against the phytopathogenic fungi belonging to the following classes: Fungi imperfecti (for example in particular Botyritis, furthermore Pyricularia, Helminthosporium, Fusarium, Septoria, Cercospora and Alternaria); Basidiomycetes (for example Rhizoctonia, Hemileia, Puccinia). Moreover, they are active against the class of the Ascomycetes (for example in particular Venturia and Erysiphe, furthermore Podosphaera, Monilinia, Uncinula) and of the Oomycetes (for example Phytophthora, Plasmopara). The compounds of the formula I can furthermore be employed as seed-dressing agents for treating of seeds (fruits, tubers, grains) and of cuttings in order to protect them from fungal infections, as well as soil-borne phytopathogenic fungi.

The invention also relates to the agents which contain compounds of the formula I in all the possible stereoisomeric forms as the active ingredient, in particular plant-protecting agents, as well as the use thereof in the agricultural sector or in related fields.

This also applies to a process for the treatment of plants which is distinguished by the application of the novel compounds of the formula I or of the corresponding novel agents.

Examples of target crops for the plant-protection use disclosed in this publication, within the scope of this invention, are the following plant species: cereals (wheat, barley, rye, oats, rice, maize, sorghum and related species); beet (sugar beet and fodder beet); pomaceous fruit, stone fruit and soft fruit (apples, pears, plums, peaches, almonds, cherries, strawberries, raspberries and blackberries; pulses (beans, lentils, peas, soya beans); oil crops (oil seed rape, mustard, poppy, olives, sunflowers, coconuts, castor, cocoa, peanuts); the gourd family (pumpkin, cucumbers, melons); fibre plants (cotton, flax, hemp, jute); citrus fruit (oranges, lemons, grapefruit, tangerines); various vegetables (spinach, lettuce, asparagus, cabbage species, carrots, onions, tomatoes, potatoes, paprika); the Lauraceae (avocado, Cinnamonium, camphor) or plants such as tobacco, nuts, coffee, pineapple, sugar cane, tea, pepper, vines, hops, the banana family and plants which yield natural rubber, as well as ornamental plants (Compositae). This enumeration does not represent any limitation.

Active substances of the formula I are customarily used in the form of compositions and can be applied to the area or plant to be treated either simultaneously or in succession with other active substances. These other active substances can be fertilizers, suppliers of trace elements or other preparations which influence plant growth. In this context, it is also possible to use selective herbicides as well as insecticides, fungicides, bactericides, nematicides, molluscicides or mixtures of a plurality of these preparations, if desired together with further carriers conventionally used in the art of formulation, surfactants or other additives which assist application.

Suitable carriers and additives can be solid or liquid and correspond to the substances advantageously used in the art of formulation, for example natural or regenerated mineral substances, solvents, dispersants. wetting agents, tackifiers, thickeners, binders or fertilizers.

A preferred method of applying an active substance of the formula I or an agrochemical agent which contains at least one of these active substances, is application onto the foliage (leaf application). In this context, the frequency of application and the dosage rate depend on the infection pressure of the specific pathogen. However, the active substances of the formula I can also enter the plant via the soil and the root system (systemic action), by drenching the site where the plant grows with a liquid preparation, or by incorporating the substances in solid form into the soil, for example in the form of granules (soil application). Compounds of the formula I can also be applied to seeds (coating), either by immersing the grains in a liquid preparation of the active substance or by coating them with a solid preparation.

In this context, the compounds of the formula I are employed in unaltered form or, preferably, together with the adjuvants conventionally used in the art of formulation. For this purpose, they are expediently processed in a known manner, for example to give emulsion concentrates, spreadable pastes, directly sprayable or dilutable solutions, dilute emulsions, wettable powders, soluble powders, dusts, granules by encapsulations, for example in polymeric substances. The application methods, such as spraying, misting, dusting, scattering, painting or watering, as well as the type of the agents, are chosen to suit the intended use and the circumstances which prevail. Advantageous application rates are generally at around 10 g to 500 g of active substance (a.s.) per hectare, preferably at around 50 g to 200 g of a.s./ha.

The preparations, i.e. the agents containing the active substance of the formula I and a solid or liquid additive, are prepared in a known manner.

Possible solvents are: aromatic and aliphatic hydrocarbons, for example xylene mixtures, cyclohexane or paraffins; also alcohols and glycols as well as their ethers, and esters, such as ethanol, ethylene glycol, ethylene glycol monomethyl ether or ethylene glycol monoethyl ether, or acetic esters; ketones, such as cyclohexanone, strongly polar solvents, such as N-methyl-2-pyrrolidone, dimethyl sulfoxide or dimethylformamide, as well as epoxidized and unepoxidized vegetable oils, such as epoxidized coconut oil or soya oil; or water.

Solid carriers which are generally used, for example for dusting agents and dispersible powders, are ground natural minerals, such as calcite, talc, kaolin, montmorillonite or attapulgite. To improve the physical properties, it is also possible to add highly-disperse silicic acid or highly-disperse absorptive polymers. Possible adsorptive, granulated granule carriers are porous types, for example pumice, ground brick, sepiolite or bentonite, possible non-sorptive carriers are, for example, calcite or sand. In addition, a large range of pregranulated materials of inorganic nature, such as, in particular, dolomite, or comminuted plant residues, can be used.

Suitable surface-active compounds are non-ionogenic or cation-active and/or anion-active surfactants having good emulsifying, dispersing and wetting properties, depending on the type of the active substance of the formula I to be formulated. Surfactants are also understood as meaning mixtures of surfactants.

Suitable anionic surfactants can be either so-called water-soluble soaps or water-soluble synthetic surface-active compounds.

More frequently, however, so-called synthetic surfactants are used, in particular alkanesulfonates, fatty alcohol sulfates, sulfonated benzimidazole derivatives or alkylsulfonates.

Possible non-ionic surfactants are polyglycol ether derivatives of aliphatic or cycloaliphatic alcohols, of saturated or unsaturated fatty acids and of alkylphenols, which can contain 3 to 30 glycol ether groups and 8 to 20 carbon atoms in the (aliphatic) hydrocarbon moiety and 6 to 18 carbon atoms in the alkyl moiety of the alkylphenols.

Further examples of non-ionic surfactants which may be mentioned are nonylphenol polyethoxyethanols, castor oil polyglycol ethers, polypropylene/polyethylene oxide adducts, tributylphenoxypolyethyleneethanol, polyethylene glycol and octylphenoxypolyethoxyethanol.

Further suitable substances are also fatty acid esters of polyoxyethylene sorbitan, such as polyoxyethylene sorbitan trioleate.

Further surfactants which are used in the art of formulation are known to those skilled in the art or can be found in the specialized literature.

As a rule, the agrochemical preparations contain 0.1 to 95% of active substance of the formula I, 99.9 to 5% of solid or liquid additive and 0 to 25% of surfactant.

While fairly concentrated agents are preferred as commercial goods, the end consumer, as a rule, uses dilute agents.

The agents can also contain further additives, such as stabilizers, defoamers, viscosity regulators, binders, tackifiers as well as fertilizers or other active substances, for obtaining specific effects.

The examples which follow are intended to illustrate the invention in greater detail without imposing any limitation. (The symbols denote: h = hour, PLC = preparative layer chromatography, TLC = thin-layer chromatography, RT = room temperature).

1. Preparation Examples

H-1. Preparation of soraphen A-5-one (Compound No. 1)

500 mg (0.84 mmol) of soraphen A etherate (M = 594.87) are dissolved in 5 ml of dichlormethane, and the solution is treated with 300 mg (1.39 mmol) of pyridinium chlorochromate. The mixture is stirred for 24 hours at room temperature and then filtered over silica gel 60 using $CH_2Cl_2$/acetone 95:5. This gives 375 mg (0.72 mmol, 86%) of the product as a pale green oil. For characterization, the crude product can be purified by means of PLC (Merck, silica gel 60, mobile phase: $CH_2Cl_2$/acetone 95:5).

In the same manner, it is possible to oxidize 9,10-dihydro-soraphen A to give the corresponding 5-oxo compound No. 2 (in Table 3).

H-2. Preparation of soraphen A-5-hydroxyimine (Compound No. 15)

60 mg (0.115 mmol) of soraphen A-5-one are dissolved in 1.5 ml of pyridine, and the solution is treated with 32 mg (0.461 mmol) of hydroxylamine hydrochloride. The mixture is stirred for 45 minutes at room temperature and then treated with ethyl acetate and semi-concentrated HCl. The organic phase is washed in succession with 5% $NaHCO_3$ solution and saturated NaCl solution, dried over $NaSO_4$ and concentrated on a rotary evaporator. This gives 56 mg of the crude product which is purified by means of PLC (silica gel 60), mobile phase: $CH_2Cl_2$/$Et_2$ 60:40, elution of the unpolar zone). Yield: 17.4 mg (0.033 mmol, 29%) of a colourless oil.

H-3. Preparation of soraphen A-5-semicarbazide (Compound No. 40)

50 mg (0.096 mmol) of soraphen A-5-one are dissolved in 1 ml of ethanol, and the solution is treated with 16 μl (16 mg, 0.20 mmol) of pyridine and 13 mg (0.116 mmol) of semicarbazide hydrochloride. After the reaction mixture has been stirred for 30 minutes at room temperature, it is substantially concentrated, and the concentrate is treated with 1N-HCl and extracted using ethyl acetate. The combined organic phases are washed using 5% NaHCO$_3$ solution and concentrated NaCl solution, dried over Na$_2$SO$_4$ and evaporated on a rotary evaporator. This gives 46 mg of the crude product which is purified by means of PLC (Merck, silica gel 60; mobile phase: dichloromethane/acetone/methanol 80:20:2; elution of the unpolar zone). Yield 16 mg (0.028 mmol, 29%)

TABLE 1

| Comp. No. | MS(EI) | | | $^1$H-NMR data of selected signals (CDCl$_3$, δ in ppm) | | | | |
|---|---|---|---|---|---|---|---|---|
| | R$_f$(Lm)* | M$^+$ | 2-H | 4-H | 6-H | 3-OH | R,X | |
| 15 | 0.29 (1) | 533 | 3.25 | ? | 1.67 | 4.01 | 7.72 (b,N—OH) | |
| 1 | 0.77 (1) | 518 | 3.23 | 3.18 | 2.56 | 4.01 | — | |
| 17 | | 547 | 3.16 | 3.20 | 1.66 | 4.02 | 3.92 (s, 3H) | |
| 40 | | 575 | 3.24 | 3.26 | 2.95 | ? | — | |
| 35 | 0.39 (1) | 532 | 3.24 | 3.45 | 2.86 | 4.01 | 5.4 (2H,b,NH$_2$) | |
| 36 | 0.49 (3) | 560 | 3.26 | 3.41 | ? | 3.91 | 2.51 (6H,-N(CH$_3$)$_2$) | |
| 42 | 0.31 (1) | | 3.16 | 3.35 | 2.70 | 3.89 | 2.42 (s, 3H)(p-tolyl) | |

*Dichloromethane/acetone (1) = 90:10
Dichloromethane/acetone (3) = 75:25

TABLE 2

| Comp. No. | $^{13}$C-MNR data of selected signals (CDCl$_3$, δ in ppm) | |
|---|---|---|
| | C-4/C-7/C-1 | C-5,R,X |
| 15 | 75.7/75.4/77.6* | 156.8 |
| 1 | 74.8/75.7/82.4* | 207.2 |
| 17 | 74.7/75.4/77.4* | 61.9,155.4 |
| 40 | 74.8/75.1/79.8* | 148.2,157.8 |
| 35 | 74.6/75.1/80.1* | 148.5 |
| 36 | 74.6/76.7/80.0* | 165.8,48.2 |

*Not assigned

H-4. Preparation of 5-(acetoyloxyimino)-soraphen A (Compound No. 49)

40 mg (77 μmol) of soraphen A-5-hydroxyimine, obtained in H-2, are dissolved in 1 ml of acetone, and the solution is treated with 50 mg of potassium carbonate and 12 mg (2 equivalents) of acetyl chloride. After the mixture has been stirred for 3 hours at RT, a TLC (mobile phase dichloromethane/acetone, 9:1 v/v; educt R$_f$0.4, product R$_f$0.7) shows that the reaction is almost complete. The solution is diluted using 10 ml of saturated ammonium chloride solution (pH 8) and extracted twice using ethyl acetate, the solvent is distilled off and the product is purified with the aid of PLC (silica gel Si 60, 1 mm, mobile phase dichloromethane/acetone, 9:1, v/v; R$_f$0.6). Yield: 18:3 mg=41% of theory.

$^1$H-NMR (CDCl$_3$): δ=2.55 (m, 1H, H-8); 3.24 (q, 1H, H-2); 3.40 (m, 1 H, H-6); 3.68 (s, 1H, H-4); 2.21 (s, 3 H, acetyl).

$^{13}$C-NMR (CDCl$_3$): δ=31.06 d, 34.91 d (C-6, C-8); 98.99 s (C-3); 163.35 s (C-5); 170.50 s (C-1); 19.68 q, 168.49 s (acetyl).

IR (film): ν=3525, 2933, 2869, 2829, 1772, 1735, 1481, 1376, 1280, 1233, 1195, 1091, 1033, 985, 919, 857, 759, 701 cm$^{-1}$.

UV (methanol): λmax (1 g ε)=202 nm (4.30).

MS (70 eV): m/e (%)=575 [4(M-H)$^+$], 543 (3), 516 (2), 484 (3), 386 (12), 259 (14), 210 (14), 208 (14), 189 (38), 157 (91), 71 (100).

Analysis: C$_{31}$H$_{45}$NO$_9$. Calculated: 575.3094 Found: 575.3100 (M-1)$^{30}$.

H-5. Preparation of 5-(benzoyloxyimino)-soraphen A (Compound No. 44)

40 mg (77 μmol) of the product obtained in H-2 are dissolved in 1 ml of acetone, and the solution is treated with 50 mg of potassium carbonate and 28 mg (2 equivalents) of benzoyl chloride. After the mixture has been stirred for 3 hours at RT, a TLC (mobile phase dichloromethane/acetone, 9:1, v/v; educt R$_f$ 0.8) shows that the reaction is almost complete. The solution is diluted with 10 ml of saturated ammonium chloride solution (pH 8) and extracted twice using ethyl acetate, the solvent is distilled off, and the product is purified with the aid of PLC (silica gel Si 60, 1 mm, mobile phase dichloromethane/acetone, 9:1, v/v; R$_f$0.65). Yield: 24.0 mg=49% of theory.

$^1$H-NMR (CDCl$_3$): δ=2.59 (m, 1H, H-8); 3.24 (q, 1H, H-2); 3.27 (s, 1H, H-4); 3.54 (m, 1H, H-6); 3.80 (s, 3-OH); 7.49, 7.61, 8.03 (benzoyl).

$^{13}$C-NMR (CDCl$_3$): δ=31.37 d, 34.88 d (C-6, C-8); 99.04 s (C-3); 163.76 s (C-5); 170.62 s (C-1); 128.72 d, 128.89 s, 129.65 d, 133.56 d, 164.61 s (benzoyl).

IR (film): ν=3527, 2960, 2933, 2871, 1737, 1481, 1280, 1239, 1181, 1129, 1087, 1021, 985, 688 cm$^{-1}$.

UV (methanol): λmax (1 g ε) =235 nm (4.25).

MS (70 eV): m/e (%) =637 [1(M-H)$^+$], 605 (1), 517 (2), 484 (3), 321 (4), 210 (14), 208 (11), 189 (35), 157 (98), 105 (100), 71 (90).

Analysis: C$_{36}$H$_{47}$NO$_9$. Calculated: 637.3251 Found: 637.3262 (M-1)$^+$.

H-6. Preparation of 5-(t-butoxyimino)-soraphen A (Compound No. 18)

52 mg (0.1 mmol) of soraphen A-5-one, obtained in Example H-1, are dissolved in 1 ml of pyridine, and the solution is treated with 20 mg of O-t-butylhydroxylamine hydrochloride (1.5 equivalents). After the mixture has been stirred for 30 minutes at 60° C., a TLC (mobile phase dichloromethane/acetone, 9:1, v/v; educt R$_f$0.65, product R$_f$0.7) shows that the reaction is complete. The solution is diluted with 10 ml of a buffer of pH 5 and extracted twice using ethyl acetate, the solvent is distilled off, and the product is purified with the aid of PLC (silica gel Si 60, 1 mm, mobile phase dichloromethane/acetone, 9:1, v/v; R$_f$0.7). Yield: 40.7 mg =69% of theory.

$^1$H-NMR (CDCl$_3$): δ=2.53 (m, 1H, H-8); 3.24 (q, 1H, H-2); 3.39 (m, 1H, H-6); 3.41 (s, 1H, H-4); 3.93 (s, 3-OH); 1.30, (s, 9H, t-butyl).

$^{13}$C-NMR (CDCl$_3$): δ=29.10 d, 35.08 d (C-6, C-8); 98.80 s (C-3); 153.22 s (C-5); 170.99 s (C-1); 27.51 q, 78.22 s (t-butyl).

IR (film): ν=3533, 2968, 2935, 2875, 2827, 1737, 1481, 1370, 1274, 1232, 1191, 1091, 1033, 977, 948, 861, 759, 699 cm$^{-1}$.

UV (methanol): λmax (1 g ε) =206 nm (4.35).

MS (70 eV): m/e (%) =589 [1(M-H)$^+$], 557 (1), 312 (1), 279 (29), 167 (71), 149 (100). 129 (60), 71 (77). 57 (90).

H-7. Preparation of 5-(allyloxyimino)-soraphen A (Compound No. 20)

52 mg (0.1 mmol) of the product obtained in H-1 are dissolved in 1 ml of pyridine, and the solution is treated with 22 mg of 0-allylhydroxylamine hydrochloride (2 equivalents). After the mixture has been stirred for 30 minutes at 60° C., a TLC (mobile phase dichloromethane/acetone, 9:1, v/v; educt $R_f$ 0.65, product $R_f$ 0.7) shows that the reaction is complete. The solution is diluted with 10 ml of 1N HCl and extracted twice using ethyl acetate, the solvent is distilled off, and the product is purified with the aid of PLC (silica gel Si 60, 1 mm, mobile phase dichloromethane/acetone, 9:1, v/v; $R_f$ 0.7). Yield: 31.2 mg = 55% of theory.

$^1$H-NMR (CDCl$_3$): $\delta$=2.53 (m, 1H, H-8); 3.24 (q, 1H, H-2); 3.32 (d, 1H, H-4); 3.45 (m, 1H, H-6); 3.99 (s, 3-OH); 4.62, 5.20, 5.28, 5.98 (allyl).

$^{13}$C-NMR (CDCl$_3$): $\delta$=29.49 d, 35.01 d (C-6, C-8); 98.86 s (C-3); 155.60 s, (C-5); 170.83 s (C-1); 74.76 t, 117.18 t, 134.35 d (allyl).

IR (film): $\delta$=3531, 2960, 2933, 2863, 2827, 1735, 1463, 1382, 1274, 1232, 1189, 1129, 1091, 1031, 968 cm$^{-1}$.

UV (methanol): $\lambda$max (1 g $\epsilon$) =205 nm (4.27).

MS (70 eV): m/e (%) =574 (8, M$^+$), 542 (8), 352 (5), 310 (5), 286 (11), 266 (14), 257 (15), 189 (18), 157 (75), 91 (95), 71 (100).

Analysis: C$_{32}$H$_{47}$NO$_8$. Calculated: 573.3301 Found: 573.3312 (M-1)$^+$.

H-8. Preparation of 5-(methoxyacetoxyimino)-soraphen A (Compound No. 12)

40 mg (77 $\mu$mol) of the product obtained in H-2 are dissolved in 1 ml of acetone, and the solution is treated with 50 mg of potassium carbonate and 22 mg (3 equivalents) of methoxyacetyl chloride. After the mixture has been stirred for 3 hours at RT, a TLC (mobile phase dichloromethane/acetone, 9:1, v/v; educt $R_f$ 0.4, product $R_f$ 0.6) shows that the reaction is almost complete. The solution is diluted with 10 ml of saturated ammonium chloride solution (pH 8) and extracted twice using ethyl acetate, the solvent is distilled off, and the product is purified with the aid of PLC (silica gel Si 60, 1 mm, mobile phase dichloromethane/acetone, 9:1, v/v; $R_f$ 0.5). Yield 16.5 mg = 35% of theory.

$^1$H-NMR (CDCl$_3$): $\delta$=2.56 (m, 1H, H-8); 3.24 (q, 1H, H-2); 3.44 (m, 1H, H-6); 3.67 (s, 1H, H-4); 4.07 (s, 3-OH); 3.27, 4.25 (methoxyacetyl).

$^{13}$C-NMR (CDCl$_3$): $\delta$=31.06 d, 34.85 d (C-6, C-8); 98.94 s (C-3); 164.34 s (C-5); 170.47 s (C-1); 56.28 q, 69.14 t, 168.37 s (methoxyacetyl).

IR (film): $\nu$=3523, 2960, 2933, 2875, 2863, 1789, 1735, 1463, 1286, 1276, 1232, 1122, 1091, 988 cm$^{-1}$.

UV (methanol): $\lambda$max (1 g $\epsilon$) =223 nm (4.79).

MS (70 eV): m/e (%) =606 (1, M$^+$), 518 (1), 502 (1), 485 (1), 417 (3), 210 (8), 189 (20), 164 (11), 157 (82), 91 (89), 45 (100).

Analysis: C$_{32}$H$_{47}$NO$_{10}$. Calculated: 605.3200 Found: 605.3201 (M-1)$^+$.

The following compounds of the formula I are obtained in this manner or following one of the procedures indicated further above.

TABLE 3

| No. | R | 9,10-position | X |
|---|---|---|---|
| 1 | CH$_3$ | DB | O |
| 2 | CH$_3$ | — | O |
| 3 | H | — | O |
| 4 | CHO | — | O |
| 5 | COCH$_3$ | — | O |
| 6 | COCCl$_3$ | — | O |
| 7 | CO—C$_6$H$_{13}$-n | — | O |
| 8 | CO-cyclopropyl | — | O |
| 9 | CO-cyclohexyl | — | O |
| 10 | CO—CH$_2$OCH$_3$ | — | O |
| 11 | COC$_2$F$_5$ | — | O |
| 12 | CH$_3$ | DB | N—O—CO—CH$_2$—OCH$_3$ |
| 13 | COCH$_2$—OCH$_3$ | — | O |
| 14 | H | — | N—OH |
| 15 | CH$_3$ | DB | N—OH |
| 16 | CH$_3$ | — | N—OH |
| 17 | CH$_3$ | DB | N—OCH$_3$ |
| 18 | CH$_3$ | DB | N—O-tert-C$_4$H$_9$ |
| 19 | CH$_3$ | — | N—OC$_6$H$_{13}$-n |
| 20 | CH$_3$ | DB | N—OCH$_2$—CH=CH$_2$ |
| 21 | CH$_3$ | DB | N—O(CH$_2$)$_4$—CH=CH$_2$ |
| 22 | CH$_3$ | DB | N—O—CH$_2$—C≡CH |
| 23 | H | — | N—O(CH$_2$)$_4$—C≡CH |
| 24 | CH$_3$ | DB | N—O—CHO |
| 25 | CH$_3$ | — | N—O—CHO |
| 26 | H | — | N—OCO—CH$_3$ |
| 27 | H | — | N—OCO—CF$_3$ |
| 28 | COCH$_3$ | — | N—OCO—CH$_3$ |
| 29 | CHO | — | N—OCHO |
| 30 | CO(CH$_2$)$_5$I | — | N—OH |
| 31 | CO(CH$_2$)$_5$—OC$_3$H$_7$ | — | N—OCH$_3$ |
| 32 | CO-cyclopropyl | — | N—OCO—C$_6$H$_{13}$ |
| 33 | CO-cyclohexyl | — | N—OH |
| 34 | CH$_3$ | DB | N—OCO—C$_4$H$_9$ |
| 35 | CH$_3$ | DB | N—NH$_2$ |
| 36 | CH$_3$ | DB | N—N(CH$_3$)$_2$ |
| 37 | CH$_3$ | DB | N—NH—CH$_3$ |
| 38 | CH$_3$ | DB | N—NH—C$_6$H$_{13}$-n |
| 39 | CH$_3$ | DB | N—NH—C$_6$H$_5$ |
| 40 | CH$_3$ | DB | N—NH—CO—NH$_2$ |

TABLE 3-continued

| No. | R | 9,10-position | X |
|---|---|---|---|
| 41 | $CH_3$ | DB | N—NH—CHO |
| 42 | $CH_3$ | DB |  N—NH—$SO_2$—C6H4—$CH_3$ |
| 43 | $CH_3$ | DB | N—NH—CO—$C_6H_{13}$-n |
| 44 | $CH_3$ | DB | N—O—CO—$C_6H_5$ |
| 45 | $CH_3$ | — | N—O—CO—$C_6H_5$ |
| 46 | —CO-tert-$C_4H_9$ | — | O |
| 47 | $CH_3$ | DB | N—O—$C_3H_7$(iso) |
| 48 | $CH_3$ | DB | N—NH—$C_3H_7$(iso) |
| 49 | $CH_3$ | DB | N—O—CO—$CH_3$ |

2. Formulation examples of the active substance of the formula I (%=per cent by weight) ["Active substance" in the following denotes an active substance from the previous Table 3]

| 2.1 Emulsion concentrates | (a) | (b) | (c) |
|---|---|---|---|
| Active substance | 25% | 40% | 50% |
| Ca dodecylbenzenesulfonate | 5% | 8% | 6% |
| Castor oil polyethylene glycol ether (36 mol of ethylene oxide) | 5% | — | — |
| Tributylphenol polyethylene glycol ether (30 mol of ethylene oxide) | — | 12% | 4% |
| Cyclohexanone | — | 15% | 20% |
| Xylene mixture | 65% | 25% | 20% |

Emulsions of any desired concentration can be prepared from such concentrates by dilution.

| 2.2 Solutions | (a) | (b) | (c) | (d) |
|---|---|---|---|---|
| Active substance | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidized coconut oil | — | — | 1% | 5% |
| Mineral oil (boiling range 160–190° C.) | — | — | 94% | — |
| (MW = molecular weight) | | | | |

The solutions are suitable for application in the form of micro droplets.

| 2.3 Granules | (a) | (b) |
|---|---|---|
| Active substance | 5% | 10% |
| Kaolin | 94% | — |
| Highly-dispersed silicic acid | 1% | — |
| Attapulgite | — | 90% |

The active substance is dissolved in methylene chloride, the solution is sprayed onto the carrier, and the solvent is then evaporated in vacuo.

| 2.4 Dusts | (a) | (b) |
|---|---|---|
| Active substance | 2% | 5% |
| Highly-dispersed silicic acid | 1% | 5% |
| Talc | 97% | — |
| Kaolin | — | 90% |

Intimate mixing of the carrier substances with the active substance gives ready-to-use dusts. With the further addition of the three carrier substances, these dusts can be ground to give dusts ready for application by containing 0.001% of active substance.

| 2.5 Wettable powders | (a) | (b) | (c) |
|---|---|---|---|
| Active substance | 25% | 50% | 75% |
| Na ligninsulfonate | 5% | 5% | —% |
| Na laurylsulfate | 3% | — | 5% |
| Na diisobutylnaphthalenesulfonate | — | 6% | 10% |
| Octylphenol polyethylene glycol ether (7-8 mol of ethylene oxide) | — | 2% | —% |
| Highly-dispersed silicic acid | 5% | 10% | 10% |
| Kaolin | 62% | 27% | — |

The active substance is thoroughly mixed with the additives, and the mixture is thoroughly ground in a suitable mill. This gives wettable powders which can be diluted with water to give suspensions of any desired concentration.

| 2.6 Coated granules | |
|---|---|
| Active substance | 3% |
| Polyethylene glycol (MW 200) | 3% |
| Kaolin | 94% |
| (MW = molecular weight) | |

In a mixer, the kaolin moistened with polyethylene glycol is evenly coated with the finely-ground active substance. In this manner, dust-free coated granules are obtained.

| 2.7 Suspension concentrate | |
|---|---|
| Active substance | 40% |
| Ethylene glycol | 10% |
| Nonylphenol polyethylene glycol ether (15 mol of ethylene oxide) | 6% |
| Na ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active substance is intimately mixed with the additives. This gives a suspension concentrate, from which suspensions of any desired concentration can be prepared by dilution with water.

3. Biological examples on plants (In the following "active substance" denotes a preparation from Table 3, unless stated otherwise).

EXAMPLE 3.1

Action against *Puccinia graminis* on wheat (a) Residual-protective action 6 days after sowing, wheat plants are sprayed with a spray liquor (0.02% of active ingredient) prepared from a wettable powder of the active substance. After 24 hours, the treated plants are infected with a uredospore suspension of the fungus. After incubation for 48 hours at 95–100% relative atmospheric humidity and about 20° C., the infected plants are placed in a greenhouse at about 22° C. The development of rust pustules is assessed 12 days after infection.

(b) Systemic action 5 days after sowing, a spray liquor (0.006% active ingredient relative to the soil volume) which is prepared from a wettable powder of the active substance, is poured to wheat plants. After 48 hours, the treated plants are infected with a uredospore suspension of the fungus. After incubation for 48 hours at 95–100% relative atmospheric humidity and about 20° C., the infected plants are placed in a greenhouse at about 22° C. The development of rust pustules is assessed 12 days after the infection.

In both experiments, fungal infestation was inhibited completely by the active substance.

In contrast, untreated, infected control plants showed infestation with Puccinia 100%.

EXAMPLE 3.2

Action against Phytophthora on tomato plants (a) Residual-protective action

After 3 weeks' growing period, tomato plants were sprayed with a spray liquor (0.02% of active ingredient) which had been prepared from a wettable powder of the active substance. After 24 hours, the treated plants were infected with a Sporangia suspension of the fungus. Fungal infestation was assessed after the infected plants had been incubated for 5 days at 90-100% relative atmospheric humidity and 20° C.

(b) Systemic action

After 3 weeks' growing period, a spray liquor (0.006% of active ingredient relative to the soil volume) which had been prepared from a wettable powder of the active substance, was poured onto tomato plants. Care was taken that the spray liquor did not come in contact with the ariel parts of the plants. After 48 hours, the treated plants were infected with a sporangia suspension of the fungus. Fungal infestation was assessed after the infected plants had been incubated for 5 days at 90–100% relative atmospheric humidity and 20° C.

In both experiments, no fungal infestation was observed during the evaluation.

EXAMPLE 3.3

Action against *Plasmopara viticola* on vines
Residual-protective action

Vine seedlings in the 4–5 leaf stage are sprayed with a spray liquor (0.02% of active ingredient) which has been prepared from a wettable powder of the active substance. After 24 hours, the treated plants are infected with a sporangia suspension of the fungus. After the plants have been incubated for 6 days at 95–100% relative atmospheric humidity and 20° C., the fungal infestation is assessed.

In contrast to the untreated, infected control plants where fungal infestation was 100%, the plants which had been treated with active substance I were free from infestation.

EXAMPLE 3.4

Action against *Cercospora arachidicola* on peanut plants
Residual-protective action Peanut plants 10–15 cm in height are sprayed with a spray liquor (0.02% of active ingredient) which has been prepared from a wettable powder of the active substance, and, 48 hours later, infected with Conidia suspension of the fungus. The infected plants are incubated for 72 hours at about 21° C. and a high atmospheric humidity and then placed in a greenhouse until the typical leaf spots occur. The fungicidal action is assessed 12 days after the infection with regard to number and size of the spots which occur.

The plants treated with active substance I showed a low degree of infestation, those plants which had been treated with one of compounds Nos. 1, 2, 12, 13, 15, 17, 18, 20, 35, 36, 40, 42, 44 and 49 were free from infestation. In contrast, untreated but infected control plants showed infestation with Cercospora of 100%. Compound No. 12 showed complete inhibition of fungal infestation (0–5% infestation), even in a dilution of 0.006%.

EXAMPLE 3.5

Action against *Venturia inaequalis* on apple shoots
Residual-protective action

Apple cuttings having fresh shoots of 10–20 cm length are sprayed with a spray liquor (0.02% of active ingredient) which has been prepared from a wettable powder of the active substance. After 24 hours, the treated plants are infected with conidia suspension of the fungus. The plants are then incubated for 5 days at 90–100% relative atmospheric humidity and placed for 10 more days in a greenhouse at 20°–24° C. Scab infestation is assessed 15 days after the infection.

The cuttings treated with active substance I were free from infestation.

EXAMPLE 3.6

Action against *Botrytis cinerea* on apple fruits
Residual-protective action

Artificially damaged apples are treated by dropwise applying a spray liquor (0.02% of active ingredient) which has been prepared from a wettable powder of the active substance, to the damaged points. The treated fruits are then inoculated with a spore suspension of the fungus and incubated for one week at high atmospheric humidity and about 20° C. In the evaluation, the damaged points which show signs of rot are counted, and the fungicide action of test substance is calculated therefrom.

Compounds Nos. 1, 2, 12, 13, 15, 17, 18, 20, 35, 36, 40, 42, 44 and 49 inhibited fungal growth completely (0–5% infestation), while the rot had spread over the control fruits.

EXAMPLE 3.7

Action against *Erysiphae graminis* on barley (a) Residual-protective action

Barley plants approximately 8 cm in length are sprayed with a spray liquor (0.02% of active ingredient) which has been prepared from a wettable powder of the active substance). After 3-4 hours, the treated plants are dusted with conidia of the fungus. The infected barley plants are placed in a greenhouse at about 22° C., and fungal infestation is assessed after 10 days.

(b) Systemic action

A spray liquor (0.006% of active ingredient relative to the soil volume) which has been prepared from a wettable powder of the active substance, is poured onto barley plants approximately 8 cm in length. Care was taken that the spray liquor did not come in contact with the aerial parts of the plants. After 48 hours, the treated plants are dusted with conidia of the fungus. The infected barley plants are placed in a greenhouse at about 22° C., and fungal infestation is assessed after 10 days.

In both experiments, the plants were free from infestation, and the control plants were completely diseased.

EXAMPLE 3.8

Action against *Rhizoctonia solani* (soil-borne fungus on rice plants)

Protective-local soil application

A spray liquor (0.006% of active ingredient) which has been prepared from a preparation of the active substance, is poured onto 12-day old rice plants without contaminating the aerial parts of the plants. In order to infect the treated plants, a suspension of mycelium and sclerotia of R. solani is placed on the soil surface. After incubation for 6 days at 27° C. (day) and 23° C. (night) and 100% relative atmospheric humidity (humid chamber) in a growth cabinet, the infestation with fungus on leaf sheaf, leaves and stem is assessed.

No infestation occurred after treatment with the active substance.

We claim:

1. Macrocyclic compound of the formula I

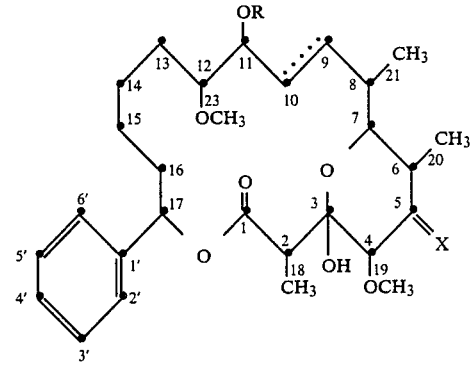

in which the dotted line in the 9,10-position is a saturated bond or a double bond, alternatively, while
R is hydrogen, $CH_3$ or —COA, where
A is hydrogen, $C_3$-$C_6$cycloalkyl or $C_1$-$C_6$alkyl which is unsubstituted or substituted by halogen or $C_1$-$C_3$alkoxy, and
X is oxygen or one of the groups =N—OY or =N—N($R_1$)($R_2$), where
Y is hydrogen, $C_1$-$C_6$alkyl, $C_3$-$C_6$alkenyl, $C_3$-$C_6$alkynyl or an acyl group —CO—Z in which
Z is phenyl, or a $C_1$-$C_6$alkyl group which is substituted by halogen or $C_1$-$C_4$alkoxy, or is hydrogen, $C_1$-$C_6$alkyl, $C_2$-$C_6$alkenyl or $C_2$-$C_6$alkynyl;
$R_1$ is hydrogen or $C_1$-$C_6$alkyl and
$R_2$ is hydrogen, $C_1$-$C_6$alkyl, phenyl, carbamoyl(-=$CONH_2$), —COA or —$SO_2$—$R_3$, where
$R_3$ is $C_1$-$C_6$alkyl or is phenyl which is unsubstituted or substituted by $C_1$-$C_4$alkyl;
with the proviso that R is methyl if there is a double bond in the 9,10-position.

2. A compound of the formula I according to claim 1, where R is hydrogen, $CH_3$ or —COA and X is oxygen.

3. A compound according to claim 2, where A is hydrogen or $C_1$-$C_3$alkyl which is unsubstituted or substituted by $C_1$-$C_3$alkoxy or monosubstituted or polysubstituted by fluorine or chlorine.

4. A compound according to claim 1, where R is hydrogen, $CH_3$ or —COA, and X is the group =N—OY, in which Y is hydrogen, $C_1$-$C_4$alkyl, $C_3$-$C_4$alkenyl, $C_3$-$C_4$alkynyl or —CO—Z, and Z is a $C_1$-$C_4$alkyl group, $C_2$-$C_4$alkenyl group or $C_3$-$C_4$alkynyl group, or is a $C_1$-$C_6$alkyl group which is substituted by fluorine, chlorine or methoxy.

5. A compound according to claim 4, where R is hydrogen, $CH_3$ or an acyl group —COA, in which A is an alkyl radical which has a maximum of 4C atoms and which is unsubstituted or substituted by halogen or alkoxy.

6. A compound according to claim 4, where R is methyl and X is the group =N—O—Y, in which Y is hydrogen, methyl, ethyl, isopropyl, allyl, propynyl, acetyl, trifluoroacetyl, trichloroacetyl or methoxyacetyl.

7. A compound according to claim 1, where R is hydrogen, $CH_3$ or —COA, and X is the group =N—N($R_1$)($R_2$), in which $R_1$ is hydrogen or $C_1$-$C_4$alkyl and $R_2$ is hydrogen, $C_1$-$C_4$alkyl or phenyl.

8. A compound of the formula I according to claim 2, selected from amongst soraphen A-5-one, soraphen B-5-one and 9,10-dihydro-soraphen A-5-one.

9. A composition for controlling or preventing plant fungal diseases comprising a fungicidally effective amount of a compound of formula I according to claim 1.

* * * * *